United States Patent
Aksenova et al.

(10) Patent No.: US 9,480,583 B2
(45) Date of Patent: Nov. 1, 2016

(54) DIRECT NEURAL INTERFACE SYSTEM AND METHOD OF CALIBRATING IT

(75) Inventors: Tetiana Aksenova, Saint-Egreve (FR); Andriy Yelisyeyev, Grenoble (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 663 days.

(21) Appl. No.: 13/698,166

(22) PCT Filed: May 17, 2010

(86) PCT No.: PCT/IB2010/001528
§ 371 (c)(1),
(2), (4) Date: Mar. 13, 2013

(87) PCT Pub. No.: WO2011/144959
PCT Pub. Date: Nov. 24, 2011

(65) Prior Publication Data
US 2013/0165812 A1    Jun. 27, 2013

(51) Int. Cl.
| | |
|---|---|
| *A61B 5/04* | (2006.01) |
| *A61F 2/72* | (2006.01) |
| *A61B 5/0482* | (2006.01) |
| *A61F 4/00* | (2006.01) |
| *G06F 3/01* | (2006.01) |
| *A61B 5/0476* | (2006.01) |
| *A61B 5/00* | (2006.01) |

(52) U.S. Cl.
CPC ............. *A61F 2/72* (2013.01); *A61B 5/04012* (2013.01); *A61B 5/0482* (2013.01); *A61F 4/00* (2013.01); *G06F 3/015* (2013.01); *A61B 5/0476* (2013.01); *A61B 5/726* (2013.01)

(58) Field of Classification Search
CPC  A61B 5/0476; A61B 5/726; A61B 5/04012; A61B 5/0482; A61F 2/72; A61F 4/00; G06F 3/015

See application file for complete search history.

(56) References Cited

U.S. PATENT DOCUMENTS

| | | | |
|---|---|---|---|
| 2003/0046254 A1* | 3/2003 | Ryu et al. | 706/15 |
| 2005/0085744 A1* | 4/2005 | Beverina et al. | 600/558 |
| 2005/0131311 A1* | 6/2005 | Leuthardt | G06F 3/015 600/545 |

(Continued)

OTHER PUBLICATIONS

Regularized tensor discriminant analysis for singel trial EEG classification in BCI. Jie Li and Liqing Zhang. Pattern Recognition Letters 31 (2010) 619-628. Available online Nov. 23, 2009.*

(Continued)

*Primary Examiner* — Christine H Matthews
*Assistant Examiner* — Joshua D Lannu
(74) *Attorney, Agent, or Firm* — Alston & Bird LLP (57) ABSTRACT

A direct neural interface system comprised of electrodes for acquiring electrophysiological signals representative of a neuronal activity of a subject's brain; a pre-processor for conditioning, digitizing and preprocessing the electrophysiological signals; a processor for processing the digitized and preprocessed electrophysiological signals and generating command signals; and an output for outputting said command signals; wherein the processor is adapted for: representing the electrophysiological signals acquired over an observation time window in the form of a N-way data tensor, N being greater or equal to three; and generating command signals corresponding to the observation time window by applying a multi-way regression model over the data tensor. A method of calibrating the direct neural interface system.

15 Claims, 3 Drawing Sheets

(56) References Cited

U.S. PATENT DOCUMENTS

2006/0265022 A1* 11/2006 John et al. .................. 607/45
2010/0234752 A1* 9/2010 Sullivan et al. ............. 600/544

OTHER PUBLICATIONS

Bro, R.; "*Multi-Way Analysis in the Food Industry: Models, Algorithms & Applications*;" retrieved on Mar. 12, 2013 from <http://www.iasbs.ac.ir/chemistry/chemometrics/history/4th/brothesis.pdf>.

Bro, R.; "*Multiway calibration. Multi-linear PLS*;" J. of Chemometrics, vol. 10, No. 1; pp. 47-61; dated Feb. 1996; retrieved on Mar. 12, 2013 from <http://www.researchgate.net/publication/229741290_Multiway_calibration._Multilinear_PLS>.

Fatourechi, M. et al.; "*A self-paced 10 brain—computer interface system with a low false positive rate*," J Neural Eng, vol. 5; pp. 9-23; doi:10.1088/1741-2560/5/1/002; dated Dec. 2007; retrieved on Mar. 12, 2013 from <ipl.ece.ubc.ca/bci_files/J3.pdf>.

Hochberg, L. R., et al.; "*Neuronal ensemble control of prosthetic devices by a human with tetraplegia*;" Nature, vol. 442, No. 7099; pp. 164-171; dated Jul. 13, 2006.

International Search Report and Written Opinion of the Searching Authority for Application No. PCT/IB2010/001528; dated Feb. 8, 2011.

Nazarpour, K., et al.; "*Parallel Space-TimeFrequency Decomposition of EEG Signals of Brain Computer Interfacing*;" Proceedings of the 14$^{th}$ European Signal Processing Conference (EUSIPCO 15 2006); dated Sep. 4-8, 2006.

Schalk, G., et al.; "*Decoding two-dimensional movement trajectories using electrocorticographic signals in humans*;" J. Neural. Eng., vol. 4; pp. 264-275; dated 2007; retrieved on Mar. 12, 2013 from <labs.seas.wustl.edu/bme/dmoran/docs/2008%20Schalk.pdf>.

Tsui, C.S.L., et al.; "*A self paced brain-computer interface for controlling a robot simulator : an online event labeling paradigm and an extended Kalman filter based algorithm for online training*;" Med Biod Eng Comput; vol. 47, No. 3; pp. 257-265; dated Mar. 2009.

\* cited by examiner

DIRECT NEURAL INTERFACE SYSTEM AND METHOD OF CALIBRATING IT

FIELD

The invention relates to a direct neural interface system, to a method of calibrating such a system and to a method of interfacing a subject's brain to an external device.

BACKGROUND

Direct neural interface systems, also known as brain-computer interfaces (BCI) allow using electrophysiological signals issued by the cerebral cortex of a human or animal subject for driving an external device. BCI have been the subject of intense research since the seventies. At present, a human subject or an animal can drive "by the thought" a simple device, such as a cursor on a computer screen. In 2006, a tetraplegic subject has even been able to drive a robotic arm through a BCI. See the paper by Leigh R. Hochberg et al. "Neuronal ensemble control of prosthetic devices by a human with tetraplegia", Nature 442, 164-171 (13 Jul. 2006).

Until now, the best results in this field have been obtained using invasive systems based on intracortical electrodes. Non-invasive systems using electroencephalographic (EEG) signals have also been tested, but they suffer from the low frequency resolution of these signals. Use of electrocorticographic (ECoG) signals, acquired by intracranial electrodes not penetrating the brain cortex, constitutes a promising intermediate solution.

Conventional BCI systems use a limited number of "features" extracted from EEG or ECoG signals to generate command signals for an external device. These features can be related e.g. to the spectral amplitudes, in a few determined frequency bands, of ECoG signals generated by specific regions of the cortex when the subject imagine performing predetermined action. As a result, only a few features of the signal are used, while the other features of the signal are not taken into account.

For example, in the paper by Schalk G., Kubanek J., Miller K. J., Anderson N. R., Leuthardt E. C., Ojemann J. G., Limbrick D., Moran D. W., Gerhardt L. A. and Wolpaw J. R. "Decoding two-dimensional movement trajectories using electrocorticographic signals in humans" J. Neural. Eng. 4 (2007), 264-75, a subject has been trained to modulate the spectral amplitude of the signals issued by a few Brodmann regions of its cortex in several frequency bands.

This approach is not completely satisfactory as, for any different command signal to be generated (e.g. vertical or horizontal movement of a cursor on a screen) it is necessary to identify different features, associated to different actions imagined by the subject and substantially uncorrelated from each other. Especially if the number of different commands signals to be generated is greater than two or three, this can get very complicated. Moreover, this approach is intrinsically inefficient as only a small amount of the information carried by the acquired ECoG signals is exploited.

The paper by K. Nazarpour et al. "Parallel Space-Time-Frequency Decomposition of EEG Signals of Brain Computer Interfacing", Proceedings of the 14$^{th}$ European Signal Processing Conference (EUSIPCO 2006), Florence, Italy, Sep. 4-8, 2006 discloses a method of processing EEG signals, based on multi-way analysis. In the method described by this paper, EEG signals are acquired by 15 electrodes disposed on a subject's scalp. The acquired signals are preprocessed, which includes spatial filtering, digitization and wavelet transform. Preprocessed data are arranged in a three-way tensor, the three ways corresponding to space (i.e. electrode location on the subject's scalp), time and frequency. A tensor corresponding to signals acquired over a 3-second observation window during which the subject imagines moving either the left of the right index is decomposed using the well-known PARAFAC (PARallel FACtors) technique. Then classification is performed using SVM Method (Support Vector Machine). As traditional classification methods, SVM enables the classification of observation vectors. This is why the tensor corresponding to signals is projected on one dimension, namely the spatial dimension, before the classification is carried out. The spatial signatures of the first two PARAFAC factors are fed to a suitable classifier which discriminates between a left index and right index imaginary movement. This method suffers from a few important drawbacks.

First of all, as only the spatial signatures of the PARAFAC factors are used, a large amount of the available information is lost. Furthermore PARAFAC is applied to decompose EEG signal tensor before and independently of classification. Being a generalization of principal component analysis (PCA), PARAFAC projects the tensor to a low dimensional space trying to explain the variability of observations (EEG), keeping the dominant (i.e. most informative) components of signal, but without taking into account their relevance for discrimination. Otherwise stated, non event-related information (useless for discrimination) can be retained, while event-related (and therefore useful for discrimination) components having low amplitude can be lost.

Moreover, a "human" intervention is still required to associate the classifier output to the left or to the right index movement. In other words, this step, the so-called calibration procedure, is not carried out automatically.

Also, only a rather narrow frequency band is considered (μ band). This band is known to be usable in EEG-based BCI. Otherwise stated, like in "classical" method there is a pre-selection of only a small portion of the available information.

Most prior art BCI systems—including the previously-described one by K. Nazarpour et al.—are based on a "cue-paced", or synchronized, approach where subjects are waiting for an external cue that drives interaction. As a result users are supposed to generate commands only during specific periods. The signals outside the predefined time windows are ignored. However, in a real-life environment this restriction would be very burdensome. As opposed to the "cue-paced" systems, no stimulus is used by "self-paced" BCIs. However, the performances of prior-art self-paced BCIs are not suitable for practical application in particular because of a high level of false system activation, which causes frustration of users and limits the application of the system. Moreover, prior art self-paced BCI experiments were carried out in laboratory conditions, which differ significantly from natural environment where users are not concentrated properly, can be disturbed by external noises, etc. In the majority of prior art self-paced experiments, session time does not exceed several minutes, which is not enough to verify BCI performance. Finally, duration of experiment series is short enough to neglect long-term brain plasticity effects. For examples of prior art self-paced BCI, see e.g.:

C. S. L. Tsui, J. Q. Gan, S. J. Roberts "A self paced brain-computer interface for controlling a robot simulator: an online event labeling paradigm and an extended Kalman filter based algorithm for online training", Med Biod Eng Comput (2009) 47:257-265

Fatourechi, R. K. Ward and G. E. Birch, "A self-paced brain-computer interface system with a low false positive rate," J Neural Eng 5:9-23. doi:10.1088/1741-2560/5/1/002.

SUMMARY

The invention aims at overcoming at least some of the drawbacks of the prior art. In particular, the invention aims at allowing better utilization of the available information, and/or at avoiding the need for human intervention for associating electrophysiological activity to intended or motor action.

An object of the present invention is a direct neural interface system comprising:

signal acquisition means for acquiring electrophysiological signals representative of a neuronal activity of a subject's brain;
preprocessing means for conditioning, digitizing and preprocessing said electrophysiological signals;
processing means for processing the digitized and preprocessed electrophysiological signals and for generating command signals as a function thereof; and
output means for outputting said command signals;
wherein said processing means are adapted for:
representing the electrophysiological signals acquired over an observation time window in the form of a N-way data tensor, N being greater or equal to two, and preferably greater or equal to three; and
generating command signals corresponding to said observation time window by the application of a multi-way regression model over said data tensor.

The multi-way regression model can result from a specific calibration procedure, which will be defined below.

In the inventive direct neural interface system, command signals are generated by applying a multi-way regression over a N-way (two-way or more, and preferably three-way or more) input data tensor. This allows efficient exploitation of the information content of the acquired signals.

In a preferred embodiment of the invention, the data tensor associated to each observation time window can be a three-way data tensor, said three ways corresponding to time, frequency and space (i.e. electrode location). Greater dimensions may be used, for example when the electrodes location is determined by two or more spatial coordinates. Conversely, the data tensor can only be two-way, e.g. if only one measurement electrode is used.

Multi-way regression can be linear. In this case, it can advantageously be based on the well-known N-way Partial Least Squares (or NPLS, or N-PLS) method. As indicated by its name, this technique is based on the minimization of a quadratic error; as it will be understood by the person skilled in the art of signal processing, alternative and more robust methods can minimize e.g. an absolute-value error.

Advantageously, the method of the invention can be carried out on EcOG signal, but this is not essential. Intracortical, EEG and even magneto-encephalographic signals could also be used.

NPLS, PARAFAC and other multi-way data analysis techniques suitable for carrying out the invention are described in the detail in the monograph "MULTI-WAY ANALYSIS IN THE FOOD INDUSTRY—Models, Algorithms & Applications>>by Rasmus Bro, freely available on the Internet at URL:
http://www.iasbs.ac.ir/chemistry/chemometrics/history/4th/brothesis.pdf.

See also: R. Bro. Multiway calibration. Multi-linear PLS. J. of Chemometrics. 1996, 10 (1): 47-61.

Another object of the present invention is a method of calibrating such a direct neural interface system, this method comprising the steps of:

a. Acquiring electrophysiological signals over a plurality of observation time windows and representing them in the form of a N+1-way tensor, called an observation tensor;
b. Acquiring data indicative of an action performed by said subject during each of said observation time windows, and organizing them in a vector or tensor, called an output vector or tensor; and
c. Determining a multi-way (e.g. multilinear) regression function of said output vector or tensor on said observation tensor.

According to an advantageous embodiment of the invention, step c. of this method can include performing multilinear decomposition of said observation tensor on a "score" vector, having a dimension equal to the number of said observation time windows, and N "weight" vectors. In particular, said "weight" vectors can be chosen such as to maximize the covariance between said "score" vector and said output vector or tensor. Even more particularly, said step c. can include performing PARAFAC decomposition of a covariance tensor representing the covariance of said observation tensor and said output vector or tensor. This decomposition gives rise to N so called "weight vectors". The observation tensor is then decomposed according to these N weight vectors.

Such a calibration method has the advantage of being carried out entirely automatically.

Still another object of the invention is a method of interfacing a subject's brain to an external device by a direct neural interface system as described above, said method comprising the steps of:

acquiring, conditioning, digitizing and preprocessing electrophysiological signals representative of a neuronal activity of said subject's brain over at least one observation time window; and
generating at least one command signal for said external device by processing said digitized and preprocessed electrophysiological signals;
wherein said step of generating command signals comprises:
representing the electrophysiological signals acquired over said or each observation time window in the form of a N-way data tensor, N being greater or equal to two (and preferably greater or equal to three); and
generating an output signal corresponding to said or each observation time window by performing multi-way regression over said or each data tensor.

This method can comprise a calibration step as described above.

The method of the invention is particularly well-suited for self-paced BCI.

BRIEF DESCRIPTION OF THE DRAWINGS

Additional features and advantages of the present invention will become apparent from the subsequent description, taken in conjunction with the accompanying drawings, which show.

DETAILED DESCRIPTION

Figure 1:
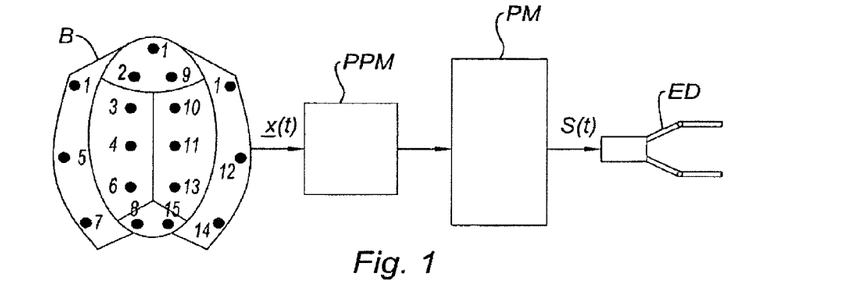
FIG. 1, a functional scheme of a direct neural interface system according to an embodiment of the invention.

FIG. 1 illustrates the general structure of a direct neural interface system according to an exemplary embodiment of the invention. In this embodiment, an intention of a (human or animal) subject to perform a simple action (e.g. press a pedal) is chosen as a specific behavior used for controlling an external device. To collect the data, the brain B of the subject is implanted with fourteen electrodes of measure (references 2-15) and three reference electrodes (reference 1). As it is commonly known, the aim of these reference electrodes is to provide a "common signal". By "common signal", it is meant an electrical signal that affects all or most of measurement electrodes. As this signal is less specific to actions, it is usually preferable to evaluate it, as precisely as possible, so as to remove it. In this purpose, one or more reference electrodes may be operated. The ECoG signals acquired by the electrodes are pre-processed by pre-processing means PPM, and then processed by processing means PM for generating command signals driving an external device ED (e.g. a manipulator). The pre-processing and processing means can be implemented in the form of application-specific integrated circuits, programmable circuits, microprocessor cards, suitably programmed general-purpose computers, etc.

Pre-processing comprises amplifying and filtering the raw signals acquired by the electrodes, sampling them at 13 KHz, converting the sample to digital format, decimating the digitized samples to a rate of 1.3 kHz. It also comprises applying a Common Average Reference (CAR) filter:

$$CAR(x_i(t)) = x_i(t) - \sum_{i=1}^{m} x_i(t)/m, \quad m=14$$

where $x_i(t)$ is the time-dependent signal acquired by the i-th electrode. The application of this common average reference yields to a reduction of a common signal measured by all electrodes.

Processing comprises performing Mayer wavelet decomposition of the preprocessed signals over sliding windows [t−Δt, t], Δt=2 sec, for the set of frequency bins f={10, 12, 14, ..., 300} Hz for all the electrodes.

As a result, each observation time window (duration of 2 seconds) is associated to a third-order (or "three-way") tensor—or "data cube"—$\underline{x}(t) \in R^{I_1 \times I_2 \times I_3}$ of independent variables. The dimension $I_1$ corresponds to the sliding window, time epoch of 2 sec. The dimension $I_2$ is determined by the range of frequency bins {10, 12, 14, ..., 300} Hz, $I_3$ is determined by number of electrodes. Time, frequency and space are also called the "modes" of analysis. In the example described below, time-frequency analysis is performed using wavelet transform.

Processing also comprises generating command signals s(t) for driving the external device ED by performing multi-way regression over each data tensor $\underline{x}(t)$ corresponding to an observation time window. This step can simply consist in unfolding said tensor in vector form and multiplying it by a "regression coefficients vector" stored in a memory device of the processing means (see below for details). The command signal generated for each observation time window can be a Boolean scalar (i.e. a on/off command), a real scalar (i.e. an analog command), a vector (e.g. for driving a movement of a multi-axis robotic arm) or even a tensor. In the specific example considered here, the command signal is a Boolean scalar, suitable for driving the (non-progressive) opening or closure of a robotic arm.

The "regression coefficients vector" (or, more generally, the regression equation applied by the processing means to generate the command signal) is determined through calibration, which is an important part of the invention.

For calibration, electrophysiological signals x(t) are acquired together with a binary signal y(t) indicating if the predetermined action has been performed by the subject. A value of y=1 indicates that the action has been performed.

If the act is performed at time t*, i.e. y(t*)=1, the elecrophysiological signal x(t) is acquired over a time window of Δt duration, said time window preferably including t*. For example, said time window can range between t*−Δt and t*. Wavelet transform of a signal during a given time windows requires the knowledge of some signals before and after said time window. In other words, the frequency analysis of the electrophysiological signal x(t) within time window [t*−Δt, t*] is performed on the electrophysiological signal x(t) stored during an extended time windows, whose duration is Δt', with Δt'=Δt+δt. For example, said extended time windows ranges between t*−Δt−δt/2 and t*+δt/2.

As a result, the frequency analysis of all signals x(t) during the temporal window [t*−Δt, t*] requires the recording of signals during the temporal window [t*−Δt−δt/2, t*+δt/2], i.e. a time span Δt' with Δt'=Δt+δt.

Based on this analysis, a tensor $\underline{x}(t)$ is built, corresponding to the temporal window Δt=2 sec.

This way, a three-way tensor $\underline{x}(t)$ is associated to each detection time t*. A Boolean variable y(t*) is also associated to time t* and to the data tensor $\underline{x}(t)$. Variable y will be called an "output" variable; actually, it is an input of the calibration algorithm, but it corresponds to the "output variable" of the multi-way regression used for generating the command signal.

This analysis is carried out when an action is performed (in this case, y(t*)=1), as well as when no action is performed (y(t*)=0). This results in data tensors $\underline{x}(t)$ which can be associated to an action (i.e. tensors x(t) with y(t)=1), and data tensors $\underline{x}(t)$ which are associated with no action (i.e. x(t) with y(t)=0).

For a relevant calibration, a few hundreds to a few thousands tensors $\underline{x}(t)$ and variables y(t) can be determined.

Figure 2:
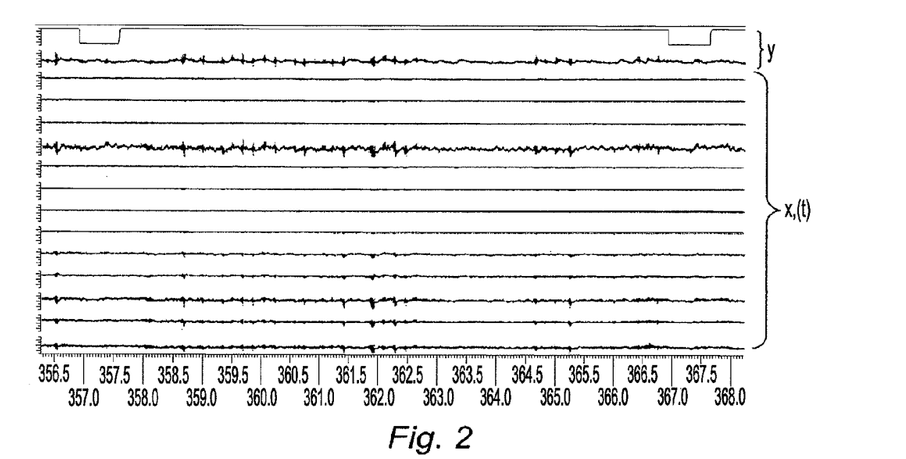
FIG. 2, a plot of the acquired electrophysiological signals.

FIG. 2 represents the neuronal signal acquired by the 14 electrodes (or "channels") and the corresponding "y" binary signal (inverted on the figure).

Figure 3:
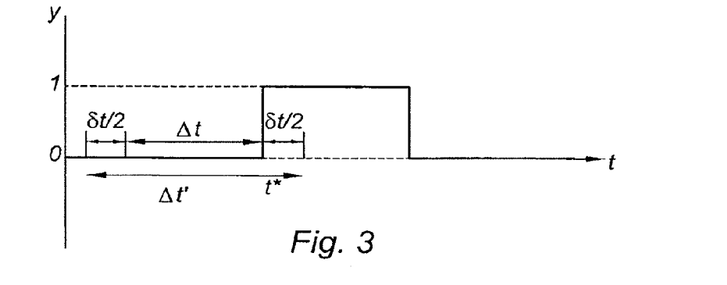
FIG. 3, a plot of a signal indicative of a voluntary action performed by said subject during the acquisition of the electrophysiological signals represented on FIG. 2.

FIG. 3 represents in detail the structure of the signal "y", showing the meaning of t*, Δt, Δt', δt.

Figure 4:
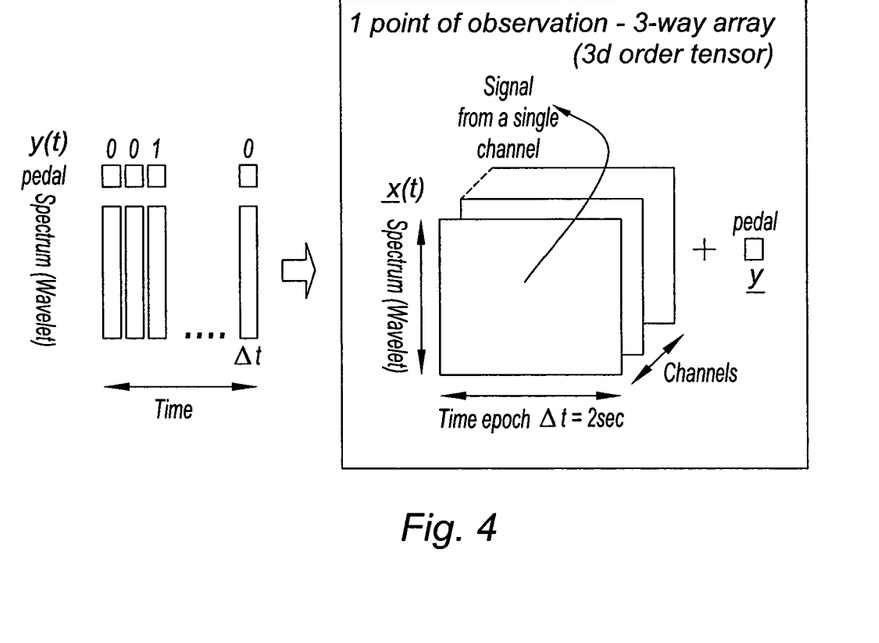
FIGS. 4 and 5, schematic illustrations of the signal representation and decomposition used in an embodiment of the invention.

FIG. 4 illustrates the data structure corresponding to one point of observation, said data structure consisting of a "data cube" $\underline{x}(t)$ and of a scalar y. It is recalled that in more complex embodiments of the invention y could be real instead of Boolean, and/or be multidimensional.

A set of "n" observations, each one corresponding to a three-way tensor x(t), forms a forth order (or four-way) tensor $\underline{X} \in R^{n \times I_1 \times I_2 \times I_3}$ and a vector y ∈ $R^n$ corresponding to the "y(t)" variable.

The overall goal of the calibration operation is the regression of variable y(t) on the tensor of observation $\underline{x}(t)$. Multilinear PLS (or NPLS) has been chosen as a preferred embodiment of the invention because of its efficiency in the case of highly correlated observations.

Partial Least Squares (PLS) is a statistical method for vector-based analyses of high dimensionality data. PLS properly treats situations when a matrix of observations X contains more variables then observations, and said variables are highly correlated. A predictive model is constructed by means of a latent variable t which is derived from X in such a way that covariance between t and dependent variables vector y is maximized. PLS is applied for both regression/classification and for dimensional reduction of the data. As opposed to other widely used projection based methods like Principal Component Analysis (PCA), PLS uses not only independent, but also dependent variables for factorization, which makes it more efficient.

NPLS is a generalization of PLS to the case of tensor independent $\underline{X}$ and/or dependent $\underline{Y}$ variables, as PARAFAC is a generalization of PCA when the order of the tensor to decompose exceeds two.

Without loss of generality, only the case of a fourth order observation tensor $\underline{X} \in R^{n \times I_1 \times I_2 \times I_3}$ and a vector $y \in R^n$ is considered in detail. Generalization is straightforward.

NPLS models tensor $\underline{X}$ by means of a "latent variable" $t \in R^n$ extracted from the first mode of $\underline{X}$ in such way that covariance between t and y is maximized. In addition to vector t, the algorithm forms a set of "weight" or "loading" vectors $\{w^1 \in R^{I_1}, w^2 \in R^{I_2}, w^3 \in R^{I_3}\}$ related to the second, the third, and the forth modality of $\underline{X}$, respectively. Finally the vector y is updated according to vector t, and this procedure is repeated a pre-defined number F of times.

Both $\underline{X}$ and y are centered along the first dimension, i.e. their mean value in time is set equal to zero.

Figure 5:
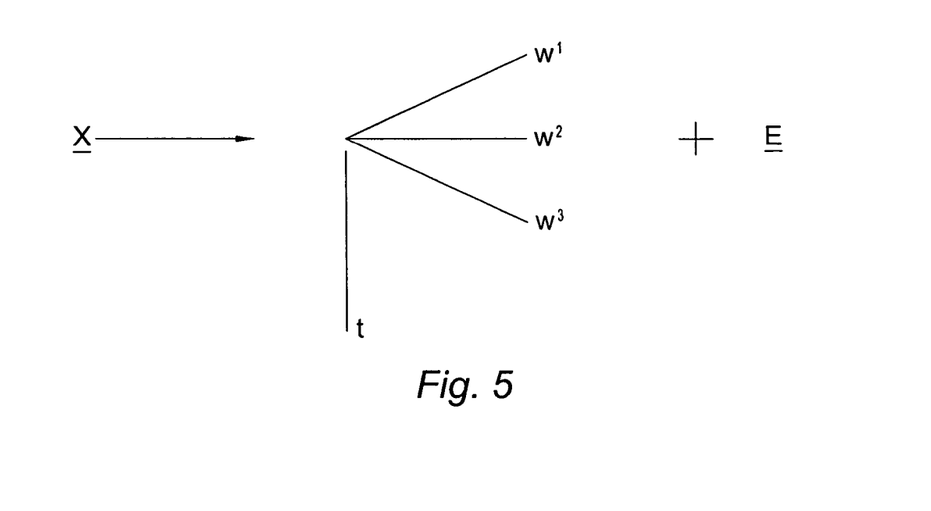

The first step of NPLS consists in decomposing $\underline{X}$ into a "score" vector $t \in R^n$ and a set of "weight" (or "loading") vectors $w^k \in R^{I_k}$, k=1,2,3. An important feature of the invention is that the weight vectors result from the decomposition of a covariance tensor $\underline{Z}$, said tensor expressing a covariance between data tensor $\underline{X}$ and y $$x_{j,i_1,i_2,i_3} = t_j w_{i_1}^1 w_{i_2}^2 w_{i_3}^3 + e_{j,i_1,i_2,i_3}. \quad (1)$$

In tensor notation $\underline{X} = t \circ (w^1 \circ w^2 \circ w^3) + \underline{E}$, where $\circ$ is the tensors product. Decomposition is generally not exact; this is accounted for by the residual tensor $\underline{E}$. This decomposition is illustrated schematically on FIG. 5.

Each weight $w^k$ corresponds to a mode of analysis: $w^1$ represents a time signature, $w^1$ represents a spectral signature ad $w^3$ represents a spatial signature.

For given set of $w^k$ $$t_j = \Sigma_{i_1,i_2,i_3} x_{j,i_1,i_2,i_3} w_{i_1}^1 w_{i_2}^2 w_{i_3}^3 \quad (2)$$

provides the least squares solution for (1) under the constrains $\|w^1\|=\|w^3\|=\|w^3\|=1$.

In matrix notation $$t = X(w^1 \otimes w^2 \otimes w^2), \quad (2^*)$$

where $\otimes$ is the Kronecker product.

The Kronecker product of vectors a and b is defined as:

$$a \otimes b = \begin{bmatrix} a_1 b \\ \ldots \\ a_n b \end{bmatrix}$$

Multilinear PLS consists in finding a decomposition (set of weights $w^k$) that maximizes the covariance between t and y. It can by formalized as the following optimization problem:

$$\max_{\|w^1\|=\|w^2\|=\|w^3\|=1} \left( \sum_{j=1}^n t_j y_j \middle| t_j = \sum_{i_1,i_2,i_3} x_{j,i_1,i_2,i_3} w_{i_1}^1 w_{i_2}^2 w_{i_3}^3 \right) \quad (3)$$

that can be written in the form $$\max_{\|w^1\|=\|w^2\|=\|w^3\|=1} \left( \sum_{i_1,i_2,i_3} z_{i_1,i_2,i_3} w_{i_1}^1 w_{i_2}^2 w_{i_3}^3 \right) \quad (4)$$

where $$z_{i_1,i_2,i_3} = \sum_{j=1}^n y_j x_{j,i_1,i_2,i_3} \quad (5)$$

Elements $z_{i_1,i_2,i_3}$ form the tensor $\underline{Z}$ which represents the covariance of $\underline{X}$ and y. Weight vectors $w^k$ are found by factorizing tensor $\underline{Z}$. To this end, the PARAFAC algorithm is applied. PARAFAC is a multi-way generalization of principal component analysis (PCA). Note that other tensor factorizing algorithms exist (see the above-referenced monograph by R. Bro) and could be applied to the invention.

PARAFAC is an iterative algorithm, which is initialized by initial weight vectors $w^k$. Random or predetermined initial vectors are used.

Residual $\underline{E}$ can also be decomposed, resulting in a second set of "score" and "weight" vectors, and so on. Each of these sets is called a "factor" of the decomposition. This iterative procedure is known as deflation.

At each deflation step, new values of dependent and independent variables are given by:

$$\underline{X}_{new} = \underline{X} - t \circ w^1 \circ w^2 \circ w^3 \text{ (i.e. } \underline{X}_{new} = \underline{E}) \quad (6a)$$

$$y_{new} = y - Tb \quad (6b)$$

where matrix $T=[t_1| \ldots |t_f]$ is composed from all score vectors obtained on the previous f steps, b is defined as: $b=(T^T T)^{-1} T^T y$ ("T" exponent means transposition, "−1" exponent means inversion). Residuals $\underline{X}_{new}$ and $y_{new}$ are used to find the next set of weights and score (loading) vectors.

In other words, $\underline{X}_{f+1} = \underline{X}_f - t_f \circ w_f^1 \circ w_f^2 \circ w_f^3$
and $y_{f+1} = y_f - T_f b_f$
The index f indicating the iteration rank ($1 \le f \le F$).

Equation (6b) provides a linear relation between output variable y and latent variables (T). A non linear equation might be applied as well.

After F steps, the regression equation becomes:

$$\hat{y} = t_1 b_1 + [t_1 t_2] b_2 + \ldots + [t_1 t_2 \ldots t_F] b_F \quad (7)$$

which can be rewritten more compactly as:

$$\hat{y} = T\hat{b} \quad (8)$$

It is to be noticed that the dimension of each vector $b_f$ is f.

In equation (8):
$\hat{y}$ is the "predictor" of y, i.e. its estimated value determined as a function of observations, $$\hat{b} = \sum_{f=1}^F b_f^F;$$

During this step, each vector $b_f^F$ is obtained from vector $b_f$ by adding the relevant number (i.e. F−f) of "0" so that the dimension of each vector $b_f^F$ is F while the dimension of each vector $b_f$ is f.

T is a matrix whose dimensions are (n, F), where n is the number of observations and F the number of iterations (and therefore the number of factors). The number of iterations F can be initially set up. It can also be found out using a cross validation procedure or another criterion known in structural modeling, for example Akaike Information Criteria.

Equation (8) can be rewritten in the form of the regression of y on $\underline{X}$. Matrix R, of dimensions $(I_1 \cdot I_2 \cdot I_3) \times F$, is defined as:

$$R = \left[ w_1 \mid (I - w_1 w_1^T) w_2 \mid \ldots \mid \prod_1^{F-1} (I - w_i w_i^T) w_k \right], \quad (9)$$

$$w_i = w_i^1 \otimes w_i^2 \otimes w_i^3. \quad (9^*)$$

It can be shown that T=XR, where matrix X is obtained by unfolding tensor $\underline{X}$ so that each line of matrix X gathers all data of each tensor $\underline{x}(t)$. If n is the temporal dimension of tensor $\underline{X}$, i.e. the number of tensors $\underline{x}(t)$ that are included in tensor $\underline{X}$, the dimension of matrix X is (n, $I_1 * I_2 * I_3$), where $I_1$, $I_2$ and $I_3$ are the dimensions of tensor x(t) as previously stated.

It follows that $\hat{y}=XR\hat{b}$. The regression coefficients vector $\hat{b}_{pls}$ is defined as $\hat{b}_{pls}=R\hat{b}$. Then, the regression equation becomes $$\hat{y}=X\hat{b}_{pls} \quad (10)$$

Equation (10) allows the use of neuronal signals to drive an external device. For each point of observation, neuronal signals are acquired and preprocessed, a tensor $\underline{x}(t)$ is formed and the predicted value of y(t) is calculated as: $\hat{y}(t)=x(t)\hat{b}_{pls}$, were x(t) is the unfolded tensor $\underline{x}(t)$. The command signal s(t) is then determined as a function of $\hat{y}(t)$, e.g. by thresholding.

In practice, it is often preferred to use equation (8) instead of equation (10). In this case, the F sets of "score" and "weight" vectors $\{w_i^1, w_i^2, w_i^3\}_{i=1,F}$ generated by PARAFAC decomposition are stored in a memory of the processing means PM, together with the F coefficients $\hat{b}$.

Deflation (equation (6)) is applied to the newly-acquired observation tensor $\underline{x}(t) \in R^{1 \times I_1 \times I_2 \times I_3}$: scalar coefficients $t_i$ are computed as $t_i = xw_i$; these coefficients form $T_{new}$ (1×F). The coefficients $\hat{b}$(F×1) are known. Then equation (8) can be applied: $\hat{y}=T_{new}\hat{b}$.

Although it makes the computation of $\hat{y}$ somehow more complex, this method is often advantageous because it is less memory consuming.

One of the main problems of the practical application of the NPLS method consists in the huge amount of data to be processed, which requires corresponding memory capacity. This problem can be mitigated by using a modified algorithm ("INPLS", for Iterative NPLS) adapted to the large data set. The main idea of this modified algorithm consists in consecutive adjustments of tensor $\underline{Z}$ factorization. It can be achieved dividing the whole training data into subsets with consecutive adjustments of the searched values. Let training data $\underline{X} \in R^{n \times I_1 \times I_2 \times I_3}$, $y \in R^n$ be divided on p subsets $\{\underline{X}^{(l)} \in R^{n_l \times I_1 \times I_2 \times I_3}, y^{(l)} \in R^{n_l}\}_{l=1}^P; \Sigma n_l = n$.

For weights vectors computation, a modified version of the PARAFAC algorithm is applied. As in the standard version of PARAFAC, numerical optimization is used for tensor $\underline{Z}$ factorization, which requires initialization. In the standard version of PLS PARAFAC, random or constant predetermined initial vectors are used for all the iteration. Instead, in the modified algorithm, previously found solutions are used as initial vectors.

The modified algorithm takes as its inputs $\underline{X}$, y, the number p of subsets $\{\underline{X}^{(l)}, y^{(l)}\}_{l=1}^P; \Sigma n_l = n$, the number F of factors. Its outputs are the F sets of weight vectors, the regression coefficients vector $\hat{b}_{pls}$ and/or the coefficients $\hat{b}$.

Let f=1 (first iteration).
1. The first set of weight vectors $w_f^1, w_f^2, w_f^3$ has to be determined.
   Let l=1 (first subset);
   The weight vectors are initialized as unit vectors $(w_f^j)^{l=1}=I$, j=1,2,3.

$$\underline{X}_{f=1}^{(l)}=X^{(l)}$$

$$y_{f=1}^{(l)}=y^{(l)}$$

Deflation:

$$\underline{X}_f^{(l)}=\underline{X}^{(l)} - \Sigma_{i=1}^{f-1} t_i \circ w_i^1 \circ w_i^2 \circ w_i^3$$

$\underline{Z}_l$, covariance tensor of $\{\underline{X}_f^{(l)}, y_f^{(l)}\}$ is computed using equation (5)

The current approximation of $w_f^1, w_f^2, w_f^3$ is computed by factorizing $\underline{Z}_l$ using $\{w_f^1, w_f^2, w_f^3\}^{l-1}$ as initialization vectors:

$$\{w_f^1, w_f^2, w_f^3\}^l = \text{TensorFactorization}(\underline{Z}_l, \{w_f^1, w_f^2, w_f^3\}^{l-1})$$

"TensorFactorization" is an algorithm which takes as its inputs $\underline{Z}_l \in R^{I_1 \times I_2 \times I_3}$, $\{w_f^1, w_f^2, w_f^3\}^{l-1}$, and training subset number l:

intermediate vectors $\{w_{current}^1, w_{current}^2, w_{current}^3\}$ are obtained by performing PARAFAC decomposition of $\underline{Z}_l$ using $\{w_f^1, w_f^2, w_f^3\}^{l-1}$ as initialization vectors;

$$\{w_f^1, w_f^2, w_f^3\}^l = (w_{current}^m + (l-1)\{w^m\}^{l-1})/l, m=1,2,3$$

Otherwise stated, $\{w_f^1, w_f^2, w_f^3\}^l$ (the weight vectors for the l-th data subset) are obtained as a linear combination of:
the weight vectors $w_{current}^m$ obtained by PARAFAC decomposition of the corresponding partial correlation tensor $\underline{Z}_l$, said decomposition being initialized by the weight vectors $\{w^m\}^{l-1}$ obtained for the previous subset; and
the weight vectors $\{w^m\}^{l-1}$ obtained for the previous subset themselves.

Using directly the $w_{current}^m$ vectors as the result of the "TensorFactorization" algorithm would result in giving excessive weight to the last data subset to be processed.

Then l is incremented, until it takes the value p, meaning that all the data subsets have been processed.

2. The last weight vectors obtained, which take into accounts all the data subsets, are normalized:

$$\{w_f^1, w_f^2, w_f^3\}^p = \{w_f^1/\|w_f^1\|, w_f^2/\|w_f^2\|, w_f^3/\|w_f^3\|\}$$

3. $t_f$ is calculated as follows:
Let i=1;
$x^f(i)$ is calculated for the current point x(i) using equation (6)
The current element $(t_f)_i$ of $t_f$ for $x^f(i)$ is calculated using equation (2)

i is incremented until it takes the value n, meaning that all the observation points have been taken into account 4. $T_f = [t_f | \ldots | t_f]$
5. $b_f = (T_f^T T_f)^{-1} T_f^T y$
6. $y_{f+1} = y_f - T_f b_f$
7. f is incremented until it takes the value F, meaning that all the required factors have been computed.
8. $\hat{b}_{pls}$ and/or $\hat{b}$ can then be computed.

Figures 6A, 6B:
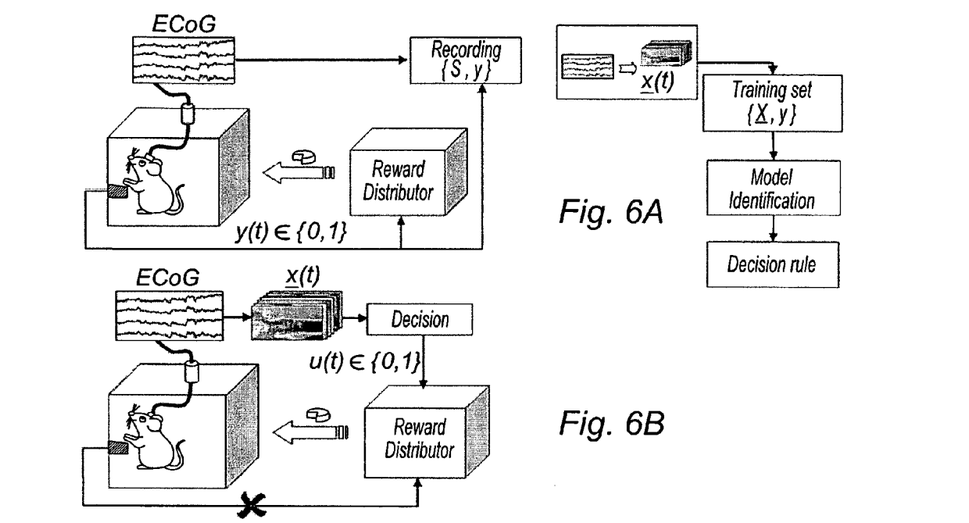
FIGS. 6A, 6B and 7 illustrate an experimental validation of the concept of invention.

The method of the invention has been tested on laboratory rats implanted with 14 electrodes (plus three reference electrodes, as shown in FIG. 1). A general scheme of the experiment is illustrated on FIGS. 6A and 6B.

Each implanted rat is free to move in a cage, and has the opportunity to push a pedal mounted on the wall of the cage. Every pushing event activates the food dispenser and the rat obtains a reward (food pellet). The rat is trained to press the pedal without any cue or conditioning stimulus.

The experiment consists of two stages. The first one is Training Stage, illustrated on FIG. 6A. During this stage, a training set of data is collected for calibration purposes. The ECoG signal x(t) and a signal y(t) indicating activation of the pedal are recorded simultaneously, the food dispenser being activated by the pedal. Data collection last up to one hour. Training sets which contain less than 50 pushes are neglected. Records are collected to be used to perform off-line calibration as described above.

During the second stage, Close Loop Real-Time BCI, the predictor ŷ is computed in real-time from acquired ECoG signal. The rat continues pressing the pedal, but it obtains the reward only when the predictor detects a pushing event.

The method was tested on the laboratory rat during more than six month. Namely three series of 5-10 experiments were carried out three months each after other. The results are summarized in the following tables. Detection rate remains very high (90% or more) for more than three months, and still exceeds 50% 6 months after calibration. The false positive rate remains very low (of the order of 1% or less) even after 6 months.

| Date | False positive amount | False positive rate | False negative amount | False negative rate | Event amount | Time, sec |
|---|---|---|---|---|---|---|
| 9 Jul. 2009 | 12 | 1.19% | 3 | 4.41% | 68 | 537.5 |
| 9 Jul. 2009 | 2 | 0.18% | 4 | 5.48% | 73 | 592 |
| 9 Jul. 2009 | 7 | 0.41% | 8 | 10.81% | 74 | 895.5 |
| 16 Jul. 2009 | 12 | 1.46% | 1 | 3.03% | 33 | 427 |
| 16 Jul. 2009 | 2 | 0.34% | 4 | 10.81% | 37 | 310.5 |
| 13 Oct. 2009 | 4 | 0.35% | 3 | 6.12% | 49 | 599.5 |
| 20 Oct. 2009 | 38 | 0.54% | 16 | 9.47% | 169 | 3600 |
| 23 Oct. 2009 | 33 | 0.94% | 13 | 11.40% | 114 | 1808.5 |
| 6 Nov. 2009 | 32 | 1.61% | 8 | 28.57% | 28 | 1005 |
| 27 Nov. 2009 | 10 | 0.77% | 21 | 38.18% | 55 | 670 |
| 1 Feb. 2010 | 38 | 1.01% | 39 | 46.99% | 83 | 1919.5 |
| 25 Feb. 2010 | 50 | 1.04% | 67 | 44.08% | 152 | 2481.5 |

Figure 7:
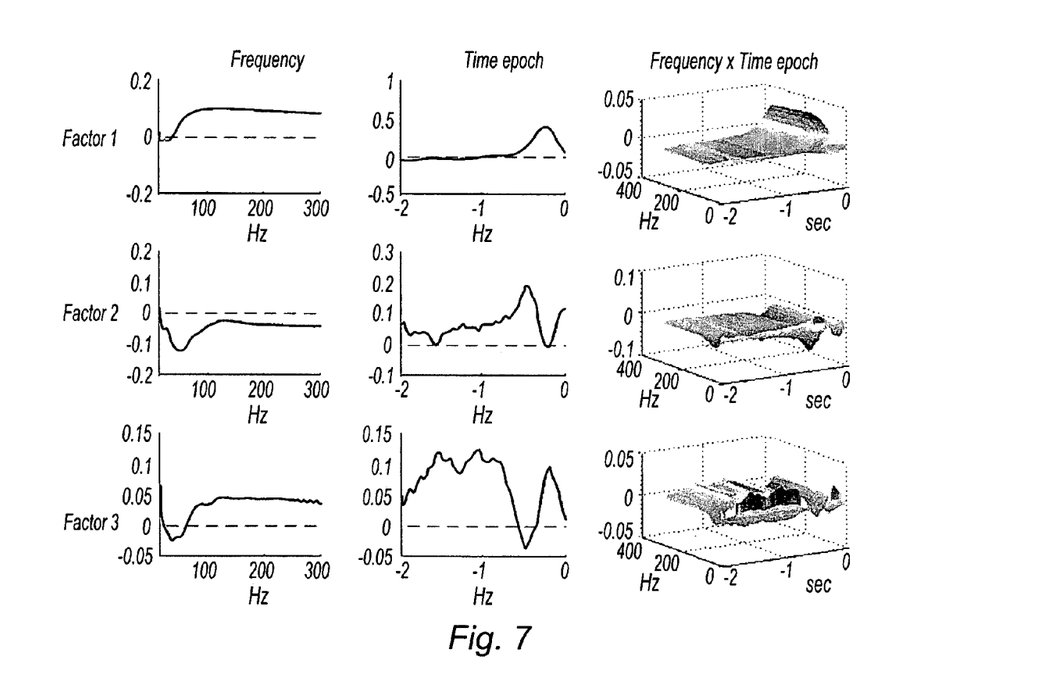

FIG. 7 illustrates the temporal and frequency modes of three of five factors which were extracted by INPLS. It can be noticed that that high frequencies give the main contribution to decision rule, as well as the time interval [−0.6, 0] seconds before the event.

The invention claimed is:

1. A direct neural interface system comprising:
    signal acquisition mechanism configured for acquiring electrophysiological signals representative of a neuronal activity of a subject's brain (B);
    preprocessor (PPM) for conditioning, digitizing and preprocessing said electrophysiological signals;
    processor configured (PM) for processing the digitized and preprocessed electrophysiological signals and for generating command signals as a function thereof; and
    output for outputting said command signals configured for driving an external device;
    wherein said preprocessor and said processor are configured for:
        generating a N-way data tensor representing the electrophysiological signals acquired over an observation time window, N being greater or equal to two; and
        generating said command signals configured for driving the external device, wherein said command signals correspond to said observation time window by applying a multi-way regression model over said data tensor, and
    wherein said processor is configured for generating an output signal corresponding to said observation time window by applying a multi-way partial least square—or NPLS—regression model to said data tensor, which allows better utilization of available information and avoids the need for human intervention for associating electrophysiological activity to intended or motor action.

2. A direct neural interface system according to claim 1, wherein said processor is configured for representing the electrophysiological signals acquired over an observation time window in the form of a three-way data tensor, said three ways corresponding to time, frequency and space.

3. A direct neural interface system according to claim 1, wherein said signal acquisition mechanism is configured for acquiring ECoG signals.

4. A method of calibrating a direct neural interface system according to claim 1, comprising the steps of:
    a. acquiring said electrophysiological signals over a plurality of observation time windows and generating a N+1-way observation tensor representing said acquired electrophysiological signals, N being greater or equal to two;
    b. acquiring data indicative of a voluntary action performed by said subject during each of said observation time windows, and organizing them in an output tensor; and
    c. determining a multi-way regression function of said output tensor on said observation tensor, wherein said steps of acquiring electrophysiological signals, acquiring data indicative of a voluntary action, and determining a multi-way regression function are performed by said direct neural interface system.

5. A method according to claim 4, wherein said step c. includes determining a multilinear regression function of said output tensor on said observation tensor.

6. A method according to claim 4, wherein said step c. includes performing multilinear decomposition of said observation tensor on a "score" vector, having a dimension equal to the number of said observation time windows, and N "weight" vectors.

7. A method according to claim 6, wherein said "weight" vectors are chosen such as to maximize a covariance between said "score" vector and said output tensor.

8. A method according to claim 7, wherein said step c. includes performing PARAFAC decomposition of a covariance tensor, representing a covariance of said observation tensor and said output tensor, yielding said "weight" vectors.

9. A method according to claim 8, wherein said step c. includes:
- c1. subdividing the observation tensor and the output tensor in a plurality of smaller tensors, each corresponding to a subset of said observation time windows;
- c2. taking a set of predetermined or random vectors as a first estimation of the "weight" vectors resulting from decomposition of said covariance tensor;
- c3. successively decomposing the subdivisions of said observation tensor, thus obtaining respective partial "weight" vectors, each decomposition being initialized by a current estimation of the "weight" vectors; and using said set of partial "weight" vectors for improving said estimation before performing a subsequent decomposition.

10. A method according to claim 4, wherein said observation tensor is a three-way data tensor, said three ways corresponding to time, frequency and space.

11. A method of interfacing a subject's brain to an external device by a direct neural interface system according to claim 1, said method comprising the steps of:
- acquiring, conditioning, digitizing and preprocessing electrophysiological signals representative of a neuronal activity of said subject's brain over at least one instance of said observation time window; and
- generating said command signals for said external device by processing said digitized and preprocessed electrophysiological signals;
- wherein said step of generating command signals comprises:
    - generating each said N-way data tensor representing the electrophysiological signals acquired over each instance of said observation time window, N being greater or equal to three; and
    - generating an output signal corresponding to each instance of said observation time window by performing multi-way partial least squares—or NPLS—regression over each said data tensor,
- wherein said steps of acquiring, conditioning, digitizing, and preprocessing electrophysiological signals and generating said command signals are performed by said direct neural interface system.

12. A method according to claim 11, comprising generating each said N-way data tensor representing the electrophysiological signals acquired over each instance of said observation time window in the form of a three-way data tensor, said three ways corresponding to time, frequency and space.

13. A method according to claim 11, wherein said electrophysiological signals are ECoG signals.

14. A method according to claim 11, comprising a calibration step comprising the steps of:
- a. acquiring said electrophysiological signals over a plurality of observation time windows and generating a N+1-way observation tensor representing the acquired electrophysiological signals, N being greater or equal to two;
- b. acquiring data indicative of a voluntary action performed by said subject during each of said observation time windows, and organizing them in an output tensor; and
- c. determining a multi-way regression function of said output tensor on said observation tensor.

15. A method according to claim 11, wherein the generation of said command signals is self-paced.

* * * * *